United States Patent
Vignon et al.

(10) Patent No.: US 10,588,595 B2
(45) Date of Patent: *Mar. 17, 2020

(54) OBJECT-POSE-BASED INITIALIZATION OF AN ULTRASOUND BEAMFORMER

(75) Inventors: Francois Guy Gerard Marie Vignon, Croton-on-Hudson, NY (US); Ameet Kumar Jain, New York City, NY (US); Jean-Luc Robert, White Plains, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 475 days.

This patent is subject to a terminal disclaimer.

(21) Appl. No.: 14/128,139

(22) PCT Filed: Jun. 19, 2012

(86) PCT No.: PCT/IB2012/053071
§ 371 (c)(1),
(2), (4) Date: Dec. 20, 2013

(87) PCT Pub. No.: WO2013/005123
PCT Pub. Date: Jan. 10, 2013

(65) Prior Publication Data
US 2014/0121502 A1    May 1, 2014

Related U.S. Application Data

(60) Provisional application No. 61/503,695, filed on Jul. 1, 2011.

(51) Int. Cl.
*A61B 8/08* (2006.01)
*A61B 8/00* (2006.01)
(Continued)

(52) U.S. Cl.
CPC ............ *A61B 8/0841* (2013.01); *A61B 8/145* (2013.01); *A61B 8/4483* (2013.01);
(Continued)

(58) Field of Classification Search
CPC .......... A61B 2034/2055; A61B 8/0841; A61B 8/145; A61B 8/4483; A61B 8/4488;
(Continued)

(56) References Cited

U.S. PATENT DOCUMENTS 5,515,853 A * 5/1996 Smith .................. A61B 5/0422
128/916
6,360,027 B1 * 3/2002 Hossack ................ A61B 8/145
348/384.1
(Continued)

FOREIGN PATENT DOCUMENTS

JP          04064348 A     2/1992

OTHER PUBLICATIONS

Cheung, S. et al "Enhancement of needle Visibility in Ultrasound-Guided Percutaneous Procedures", Ultrasound in Medicine and Biology, vol. 30, No. 5, May 2004, pp. 617-624.
(Continued)

*Primary Examiner* — Amelie R Davis

(57) ABSTRACT

A device and method for initializing an ultrasound beamformer to image an object based on a tool-pose-estimation of the object include an ultrasound imaging array and an object. The ultrasound imaging array operates with the beamformer. The object has a sensor external to the ultrasound imaging array. The tool-pose-estimation includes an estimation of the location and/or the orientation of the object. The tool-pose-estimation of the object is derived by a processor that receives an output of the sensor disposed on the object external to the imaging array that operates with the beamformer. The processor supplies the tool-pose-estimation to
(Continued)

the beamformer to initialize the beamformer using the tool-pose-estimation for operating the imaging array.

20 Claims, 6 Drawing Sheets

(51) Int. Cl.
*G01S 15/89* (2006.01)
*G01S 7/52* (2006.01)
*A61B 34/20* (2016.01)
*A61B 8/14* (2006.01)
*A61M 25/01* (2006.01)
*A61B 90/00* (2016.01)

(52) U.S. Cl.
CPC ............ *A61B 8/4488* (2013.01); *A61B 8/463* (2013.01); *A61B 8/5269* (2013.01); *A61B 8/585* (2013.01); *A61B 34/20* (2016.02); *A61M 25/0108* (2013.01); *G01S 7/52047* (2013.01); *G01S 15/899* (2013.01); *G01S 15/8997* (2013.01); *A61B 2034/2051* (2016.02); *A61B 2034/2055* (2016.02); *A61B 2090/378* (2016.02)

(58) Field of Classification Search
CPC ....... A61B 8/463; A61B 8/5269; A61B 8/585; A61B 34/20; A61B 2090/378; A61B 2034/2051; A61B 2034/20255; A61M 25/0108; G01S 15/899; G01S 15/8997; G01S 7/52047

See application file for complete search history.

(56) References Cited

U.S. PATENT DOCUMENTS

| | | | |
|---|---|---|---|
| 7,744,532 B2 | 6/2010 | Ustuner | |
| 7,772,541 B2 | 8/2010 | Froggatt | |
| 7,933,007 B2 | 4/2011 | Stanton | |
| 2002/0173719 A1 | 11/2002 | Zhao | |
| 2002/0173720 A1 | 11/2002 | Seo | |
| 2002/0183592 A1 | 12/2002 | Suzuki | |
| 2003/0060700 A1 | 3/2003 | Solf | |
| 2003/0187354 A1* | 10/2003 | Rust | A61B 8/00 600/437 |
| 2004/0101706 A1 | 5/2004 | Bohm | |
| 2007/0118140 A1* | 5/2007 | Baur | A61B 17/152 606/87 |
| 2009/0093719 A1 | 4/2009 | Pelissier | |
| 2010/0168556 A1 | 7/2010 | Shen | |
| 2010/0194879 A1 | 8/2010 | Pasveer | |
| 2013/0158405 A1* | 6/2013 | Bagge | G01S 7/52068 600/447 |

OTHER PUBLICATIONS

Ayvaci, Alper et al "Biopsy Needle Detection in Transrectal Ultrasound", Computerized Medical Imaging and Graphics, vol. 35, No. 7, May 2011.

* cited by examiner

OBJECT-POSE-BASED INITIALIZATION OF AN ULTRASOUND BEAMFORMER

CROSS-REFERENCE TO PRIOR APPLICATIONS

This application is the U.S. National Phase application under 35 U.S.C. § 371 of International Application No. PCT/IB2012/053071, filed on Jun. 19, 2012, which claims the benefit of U.S. Provisional Patent Application No. 61/503,695, filed on Jul. 1, 2011. These applications are hereby incorporated by reference herein.

FIELD OF THE INVENTION

The present invention is directed to using ultrasound in imaging an object and, more particularly, to initializing a beamformer for this purpose based on an estimate of the location and/or orientation of the object.

BACKGROUND OF THE INVENTION

Precise visualization of catheters and needles, and real-time knowledge of their localization with respect to the anatomy, are needed for minimally invasive interventions. Intra-operative ultrasound is often used for these purposes.

However, many surgical tools are difficult to image with conventional pulse-echo ultrasound. Also, visualization is often incomplete or artefact-prone.

For instance, the usability of 3D Transoesophagial Echocardiography (3D-TEE) for guidance of catheter cardiac interventions is still limited because it is challenging to image catheters reliably with ultrasound.

Catheters and needles are specular reflectors that reflect the sound away from the imaging probe if the insonifying angles are not favorable.

As a consequence, a catheter appears on and off on 3D-TEE images during its progression through the cardiac chambers. It also frequently happens that some parts of the catheter are visible and others not depending on the local angle between the catheter and the imaging beams. For instance the distal end of the catheter may be invisible and some point along its shaft may be mistaken as its tip. Also, due to weak reflection, signal from the catheter may be drowned in signal from the surrounding anatomy.

It is also difficult to image intravenous catheters.

Likewise, needles, often used for biopsy, nerve block, drug delivery, hyperthermic therapy, and radiofrequency (RF) ablation, etc., are hard to visualize, especially when thin and applied to deep tissue locations. Visibility greatly improves if the insonifying angle is perpendicular to the needle. However, achieving a favorable angle is usually limited to shallow needle insertions. In addition, due to tissue heterogeneities and asymmetric needle bevel, the needle often deviates from its planned trajectory, even when a needle guide is used. If the needle deviates from the imaged plane, it becomes invisible. Very often, the clinician jiggles the needle to see on the image display where it is located.

Electromagnetic (EM) sensors have been attached to the interventional tool and the ultrasound probe, to determine the tool pose, i.e., location and orientation, in the acquired image (SonixGPS Specifications Sheet, UltraSonix, available at the World Wide Web at ultrasonix.com/webfm_send/117).

In a technique proposed in a paper entitled "Enhancement of Needle Visibility in Ultrasound-Guided Percutaneous Procedures, by Cheung et al., Ultrasound in Medicine and Biology, Vol. 30, No. 5 (2004), the ultrasound probe is used to determine the tool pose. Beamforming parameters are created, based on the determination, to insonify the tool at a better angle.

SUMMARY OF THE INVENTION

The present invention is directed to addressing one or more of the above concerns.

In an aspect of the present invention, an estimate is derived of a location and/or orientation of an object. A beamformer is initialized with the estimate. The beamformer operates with an ultrasound transducer array in imaging the object. The estimate is based on output of at least one sensor external to the array and disposed with respect to the object for sensing the location/orientation.

According to another aspect, the estimate is made without the need for a result of any imaging based on data arriving by reflected ultrasound.

In one aspect, at least one of the sensors is attached to the object.

As a sub-aspect, at least two of the sensors, located mutually apart, are attached to the object.

In a different aspect, the object has an elongated body, and the at least one sensor conforms to at least a portion of the body for sensing a shape of the portion in determining the orientation.

In an alternative aspect, one or more of the sensors is an electronic device.

In a yet different aspect, one or more of the sensors is an ultrasound sensor.

In another aspect, a tool comprising the object is rigid and has a base. The at least one sensor is configured for optically detecting the base to afford the deriving of the estimate.

In a related aspect, the beamformer is configured for limiting an angle of incidence of a transmit beam, a receive beam, or both, to a nonzero value to avoid sidelobe and reverberation artefacts.

In one other related aspect, the beamformer is configured for using the estimate to optimize the beamforming.

In an additional aspect, the beamformer is configured for, based on the estimate, placing a transmit focus at the object.

In a sub-aspect of the above, the estimate is of the location and the orientation, the object is elongated, and the beamformer is further configured for, based on the estimate, placing a plurality of transmit foci along the object at different depths to conform to the object.

In one version, the object is elongated, and the beamformer is configured with steering capability in an elevation direction. The initializing is directed to forming an imaging plane in which at least a tip of the object longitudinally extends.

As a sub-aspect of the above version, at least the tip currently longitudinally extends within another imaging plane, the planes being mutually non-parallel. The beamformer is further configured for imaging both planes for concurrent display in real time.

In a different aspect, the object is elongated, and the beamformer is configured for beam spacing that is spatially fine enough to mitigate or eliminate imaging artefacts discernible as interruptions along the object.

As yet another aspect, the estimate includes an estimate of the location, the location being of a tip of the object.

In a complementary aspect, the estimate includes an estimate of the orientation.

In one additional aspect, the deriving, and beamforming by the beamformer, are performed in real time to track the object.

As a yet further aspect, the deriving includes calculating the estimate.

In yet another aspect, the object is a specular reflector of ultrasound.

In some embodiments, a device for performing the above-described functionality is configured as one or more integrated circuits.

In some versions, an estimate is derived of at least one of a location, and an orientation, of an object. A beamformer is initialized with the estimate. The beamformer operates with an ultrasound transducer array. The estimate is based on electromechanically-induced ultrasound that arrives at the array by transmission rather than by reflection.

Details of the novel, tool-pose-based ultrasound beamforming initialization technology are set forth further below, with the aid of the following drawings, which are not drawn to scale.

DETAILED DESCRIPTION OF EMBODIMENTS

According to one embodiment for imaging an interventional tool, ultrasound transducers attached to the tool are used in one-way only beamforming.

Figure 1A:
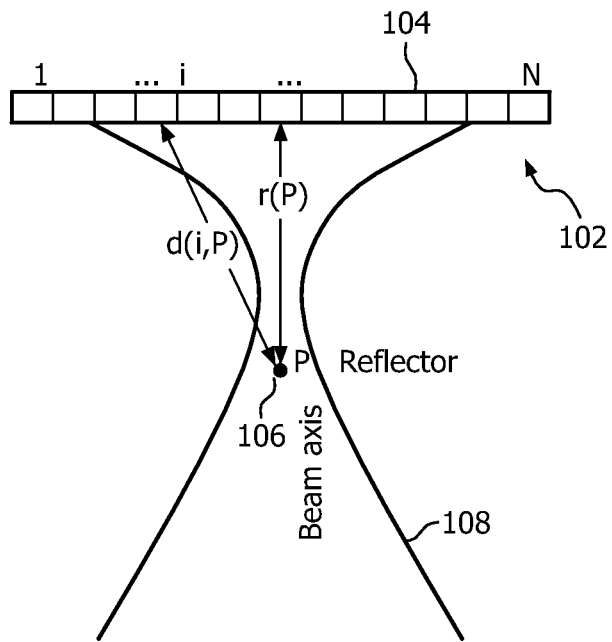
FIGS. 1A, 1B are conceptual diagrams for comparing between two-way beamforming and one-way only beamforming.
Figure 1B:
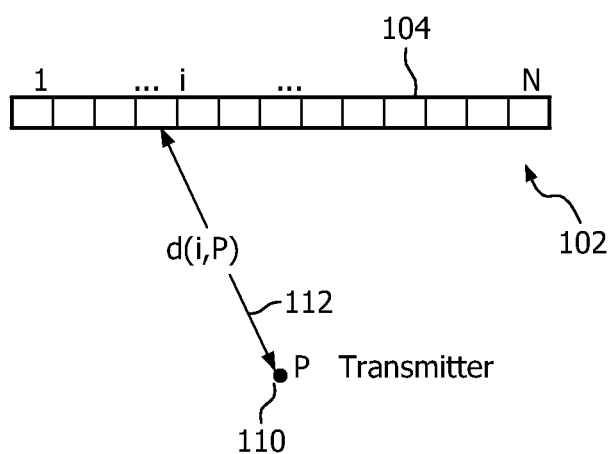

FIGS. 1A, 1B offer, by way of illustrative and non-limitative example, a comparison between two-way beamforming and one-way only beamforming FIG. 1A, representative of two-way beamforming shows an imaging array 102 of N elements 104 issuing ultrasound that impinges on a reflector 106. Since the ultrasound waves go out and back (from the imaging array to the reflectors and back to the imaging array), this is describable as "two-way" or "round-trip" beamforming. On receive (of the ultrasound that has reflected back), beamforming determines the reflectivity of the reflector 106 and the position of the reflector relative to the array 102. Here, it is assumed that the reflector 106 is in the imaging plane of the array 102, but the same principles apply for three-dimensional beamforming with a two-dimensional array. The array 102 sends out a beam 108 that reflects off reflector 106 and returns to all elements 104 of the array 102. The flight of the pulse is over a distance r(P)+d(i,P) for element i. Each element 104 measures continually the amplitude of the return ultrasound. For each element 104, the time until a maximum of that measurement, i.e., the "round-trip time of flight," is indicative of the total flight distance. From these measurements, the relative position of the reflector 106 is computed geometrically. As to the reflectivity of the reflector 106, it can be indicated by summing the received traces over all i (i.e., over all elements 104) after applying the adequate time delays corresponding to point P.

As seen from FIG. 1B, ultrasound generated by an ultrasound transducer in one-way only (receive) beamforming does not take account of an echo. Instead, as illustrated here, the ultrasound transducer acting as a transmitter 110 emits a pulse 112 which is incident on each element 104 of the array 102. Thus, the beamforming is based on ultrasound that arrives by transmission rather than by reflection. The flight here of the pulsed ultrasound upon which imaging is based is, in contrast to the two-way beamforming case, over the distance d(i,P). The time from emission of the pulse 112 until the maximum amplitude reading at an element 104 determines the value d(i,P) for that element i. Thus, the position of the transmitter 110 can be derived geometrically, and the reflectivity calculated by summing the received traces over all i after applying the adequate time delays.

Although one-way beamforming is implementable in the time domain via delay logic, as discussed hereinabove, it can also be implemented in the frequency domain by well-known Fourier beamforming algorithms.

Figure 2A:
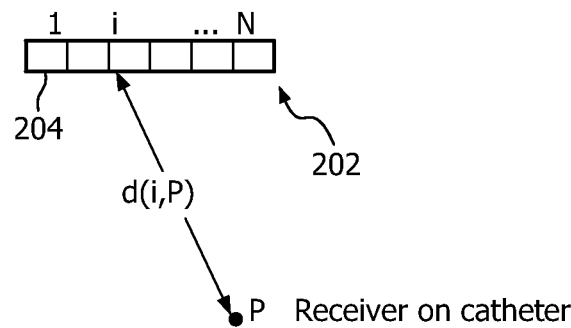
FIGS. 2A, 2B are conceptual diagrams that portray, correspondingly, a synthetic aperture acquisition scheme and the same scheme using virtual transducers.
Figure 2B:
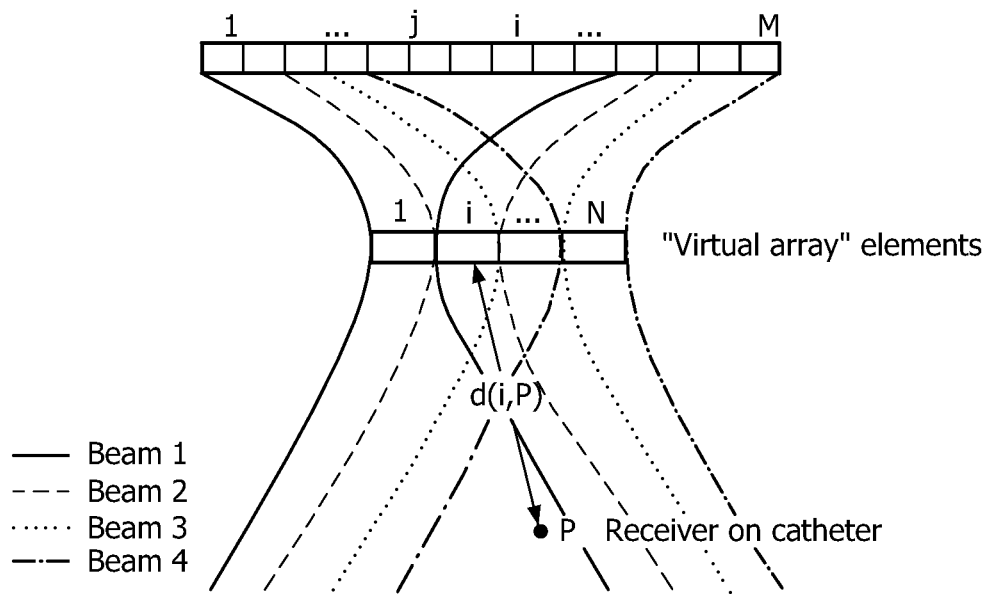

FIGS. 2A, 2B portray, respectively, a synthetic aperture acquisition scheme and the same scheme using virtual array elements. Both schemes are utilizable in aspects of the invention.

Turning now to FIG. 2A, for an imaging array 202, each of the N elements 204 sequentially sends out an impulse, i.e., pulse, into the medium. Let $r_{i,P}(t)$ be the temporal signal received by the receiver P (on a catheter, needle, or other interventional tool) when element i fires an impulse. (The origin of time is taken each time an element is fired.) It is assumed that the receiver P is in the imaging plane of the array, but the same principles apply for three-dimensional beamforming with a two-dimensional array. The travel time from i to P is $$t_{i,P} = d(i,P)/c \quad \text{(equation 1)}$$

where d(i,P) is the distance between element i and receiver P, and c is the medium's speed of sound. Thus $r_{i,P}(t)$ has its maximum at $t_{i,P}$. An image of the receiver in space is formed by, for each point Q inside the field of view, taking the summation:

$$s(Q) = \Sigma r_{i,P}(t_{i,Q}) \quad \text{(equation 2)}$$

over i=1 to N. Apodization functions may optionally be used as is standard practice in the art.

The quantity s(Q) will be maximized for Q=P; that is, at the location of the receiver.

Referring now to FIG. 2B, the retrospective dynamic transmit (RDT) with virtual array elements scheme shown is similar to above-described synthetic aperture scheme—the imaging array is replaced by a "virtual array" made of "virtual elements." Each virtual element is the focal location of one focused beam emanating from the real (physical) imaging array. There are as many virtual elements as there are focused beams from the imaging array. The imaging array sends out N beams into the medium, sweeping the field of view. Let $r_{i,P}(t)$ be the temporal signal received by the receiver P in the medium when the beam number i is fired into the medium (i.e., the virtual element i emits an impulse).

The origin in time is now taken when the beam is emitted. The travel time from virtual element i to P is $$t_{i,P} = d(i,P)/c \quad \text{(equation 3)}$$

The time it takes for the transmitted beam to focus at the location of the virtual array element is $$t_i = d(i)/c \quad \text{(equation 3)}$$

where d(i) is the distance between the center of the imaging array's active aperture and the focal point of transmit beam i (i.e., the virtual transducer i). In usual transmit schemes, all transmits are focused at the same depth, so d(i) does not depend on i; let us call it $d_1$ and $$t_1 = d_1/c \quad \text{(equation 4)}$$

It thus takes the time $t_1 + t_{i,P}$ between the emission of beam i and reception of the corresponding impulse at point P. The quantity $r_{i,P}(t)$ thus has its maximum at $t_1 + t_{i,P}$.

An image of the receiver in space is formed by, for each point Q inside the field of view, doing the summation:

$$s(Q) = \Sigma r_{i,P}(t_1 + t_{i,Q}) \quad \text{(equation 2)}$$

over i=1 to N.

The quantity s(Q) will be maximized for Q=P which is the location of the receiver. As in the synthetic aperture case described earlier, weights can be applied to the different terms of the sum of equation (2), giving more importance to some beams and less importance to others. The optimal weight design is well-known in the art.

In reality, since the virtual array elements are not punctual and have a certain directivity that is governed by the shape of the actually transmitted imaging beams, it is necessary, as well-known in the art, to perform some transmit beam simulations to compute the exact theoretical arrival times of each beam i at each point Q.

Use of retrospective dynamic transmit (RDT) with virtual array elements affords optimal (diffraction-limited) resolution of the tracked object at all depths.

Figure 3A:
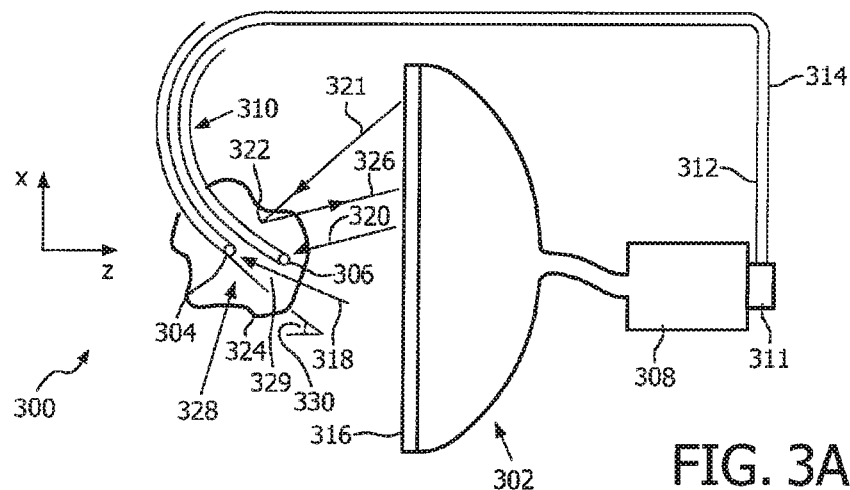
FIGS. 3A-3C are schematic diagrams of exemplary ultrasound transducer and shape sensor embodiments.

FIG. 3A depicts, by way of illustrative and non-limitative example, an ultrasound imaging device 300. It includes an ultrasound imaging probe 302; ultrasound sensors (i.e., electronic devices that include transducers acting as receivers) 304, 306. The sensors 304, 306 are external to, i.e., separate and apart from, the probe. The device 300 also includes a beamformer 308; a catheter, needle or other tool 310 along which the sensors are attached or otherwise placed; an estimation and initialization module 311 for making or calculating a tool pose estimate and supplying it to the beamformer 308 to initialize the beamformer; and wire inputs 312, 314 from the sensors to the module 311. Alternatively, the sensors 304, 306 and the module 311 might be implemented for communicating wirelessly with each other. The probe 302 includes a transducer array 316 which operates with the beamformer 308 in imaging. The probe is two-dimensional (2D), or 1.75D, and is capable of three-dimensional (3D) imaging, although a one dimensional array can be used for 2D imaging. The lateral direction, denoted "x", and the axial direction, denoted "z", are in the plane of the drawing.

The beamformer 308, or a component thereof which may operate according to RDT discussed above, provides one-way-only beamforming of signals that arrive from the wire input 312, 314. The one-way beamforming is represented in FIG. 3 by the arrow 318 from the transducer array 316 to the ultrasound sensor 304 shown on the left, and by the arrow 320 from the array to the other sensor 306. The one-way beamforming is based for example on element-by-element emission in scanning the transducer array 316 and the arrival of the emitted ultrasound at the sensors 304, 306.

The beamformer 308 also performs two-way beamforming which is 2D here, but may be 3D. In the lateral direction, 2D imaging provides a "slice" referred to herein as the target plane. A transmit beam 321 is represented by the arrow from the array 316 to a point 322 in a region of interest 324. The corresponding receive beam 326 is represented by the arrow back to the array 316.

All points 322 in a 3D region of interest 324 are insonified and processed in the imaging.

Likewise, all sensors, here both sensors 304, 306, are utilized in respective one-way beamforming operations.

Within the region of interest 324 is a tip 328, of the catheter 310, which resides, at any given moment, at a respective location 329 and orientation 330 (only one angular component being shown in this drawing view), i.e., a point and a direction, respectively, in 3D space. The location 329 and orientation 330 (or "pose") are determined on-the-fly based on the known attachment points of sensors 304, 306 to the tool, and on the spatial positions of the sensors calculated by the beamformer 308 based on the one-way only beamforming. A separate one-way beamforming result is obtained for each of the sensors 304, 306. The beamforming localizes the sensor 304, 306 in the region of interest 324 in the same coordinate system as the regular pulse-echo image of the region of interest. By inclusion within the catheter 310, the sensors 304, 306 are disposed with respect to it for sensing its location and/or orientation. Optionally for instance, merely the location 329 of the catheter 310, for example of the tip 328, may be derived from the output of a given sensor 304, 306 onboard the catheter. Notably and in any event, the pose estimate is made without the need for a result of any imaging based on data arriving by reflected ultrasound.

In one embodiment, tissue-specific frames (with beamforming and other parameters (pulse length, frequency, filters . . . ) optimized for viewing the anatomy are alternated, or otherwise interspersed, with tool-specific frames (with adaptively determined optimal beamforming parameters optimized, by the novel techniques herein, for the tool content of the frame). Both types of frames fall under the category of pulse-echo acquisition (or "imaging") frames.

An initialization frame, on the other hand, is acquired by scanning the transducer array 316 with the sensors 304, 306 switched into receive mode at the appropriate moments, as described in further detail below. These frames are used to make the tool pose estimate for initializing the beamformer 308 with respect to tool-specific frames.

Initialization and pulse-echo image acquisition are separated by means of frequency or by means of timing (e.g., alternating, or otherwise interspersing, imaging frames with initialization frames). The sensors 304, 306 are triggered active in receive (to, in other words, start the clock at time zero in measuring the one-way delay) by the line trigger of a scanner (not shown) that incorporates the probe 302 and the beamformer 308. A trigger signal is emitted each time the probe 302 emits a different transmit beam. The tissue-specific and tool-specific frames are combined, as discussed in more detail further below, in forming one or more display images. The dynamic range of the initialization frame can be made half that of the imaging frame to take into account one-way beamforming only that induces sidelobes roughly twice as high as conventional two-way imaging.

Although the ultrasound imaging device 300 is described herein above as implemented with ultrasound sensors 304, 306 as receivers, the transducers can alternatively be configured as ultrasound transmitters 110. They operate electromechanically, as in the case of a piezoelectric element, and are as omnidirectional as possible. The same separation, by time or frequency, of tool-pose-estimation (or "initialization") acquisition and imaging acquisition mentioned above in connection with receivers applies also in the case of transmitters. As to frequency separation, the transmitter (or "tracked source") 110 is able to emit short pulses (optionally, more complicated waveforms with transmit codes) which can (but do not necessarily) have a frequency band different from that of the imaging pulses of the intra-operative imaging ultrasound, in order to avoid interference between the initialization and imaging pulses. Reception of initialization and imaging pulses may be differentiated either simply with receive filters or more sophisticated pulse signature identification algorithms.

In addition, in the case of transmitters 304, 306, they are also separated, for initialization frame purposes, by time or frequency. The separation distinguishes the radiofrequency data of one transmitter from the other, for their separate localizations.

Propagation of sound occurs from the transmitter 110 to the individual elements 102 of the transducer array 316. Because of reciprocity, the transmitter 110 that sends signals toward individual elements 104 of the ultrasound scanner can, in an analogous sense, replace the ultrasound receiver, discussed in the previous embodiment, that receives signals from individual elements of the ultrasound scanner, without changing the signal processing for its localization. The transmitter 110, like the receiver 304, 306, can be precisely imaged by adjusting the ultrasound scanner's beamforming delays to account for the one-way only propagation of transmissive ultrasound between the tracked ultrasound transmitter(s) 110 and the transducer array 316. The device used to sense signals from the transmitter 110 is the same ultrasonic probe 302 (e.g., a 2D probe for 3D tracking) and scanner that are used to make the intra-operative ultrasound anatomical images that are obtained from some combination of the tissue-specific and tool-specific frames.

The scanner triggers emission of sound from the transmitter(s) 110 with its line trigger (which is designed to be fired upon emission of each beam) or frame trigger (which is designed to be fired upon emission of each frame), propagation of sound then occurring from the transmitter(s) to the individual elements 104 of the transducer array 316.

Alternatively, the transmitter 110 can be the one that triggers image acquisition by the ultrasound scanner. This might be desirable in the case where the duty cycle and on/off times of the transmitter(s) on the surgical tool 310 have been optimized for best treatment safety and efficacy (in the case where the transmitter is actually used for treatment). In effect then, the ultrasound imaging device 300 is configured for an ultrasound scanner triggering, by a line trigger or by a frame trigger, emission of sound from the transmitter(s) 110 and/or for the transmitter(s) triggering the scanner active for image acquisition.

The ultrasound scanner can be modified for tracking the transmitter 110 by adjusting its receive beamforming delays, e.g., $[r(P)+d(i,P)]/c$ as in FIG. 1, to account for the one-way only ultrasound propagation (from the transmitter(s) to the probe 302).

The ultrasound scanner alternates imaging frames (active ultrasound emission from the imaging probe 302, the transmitter(s) 110 on the interventional tool 310 are turned off, and conventional two-way beamforming is performed for pulse-echo imaging) with initialization frames (emission from the imaging probe is turned off, the transmitter(s) on the interventional tool are turned on, one-way only beamforming is performed). Optionally, if the transmitter(s) 110 are designed with a different frequency from the imaging frequencies, there is no need to turn on/off the transmitter/imaging probe during the imaging or initialization frames: for the initialization frames, the temporal receive filters are just modified to take into account the different nominal frequency of the transmitter(s) 110.

In an alternative, manual embodiment of the ultrasound imaging device 300, the pose estimate can be derived, instead of on-the-fly, responsive to selection by the user from among candidate poses. Each candidate is associated by software in the beamformer 308 with preset beamforming parameters. The user manually chooses the candidate that is thought to best match the current intervention geometry. The chosen candidate is supplied, and derived by the estimation and initialization module 331 for subsequent output to the beamformer 308.

The estimation and initialization module 311 may be implemented as one or more integrated circuits for deriving the estimate and using the derived estimate to initialize the beamformer.

Figure 3B:
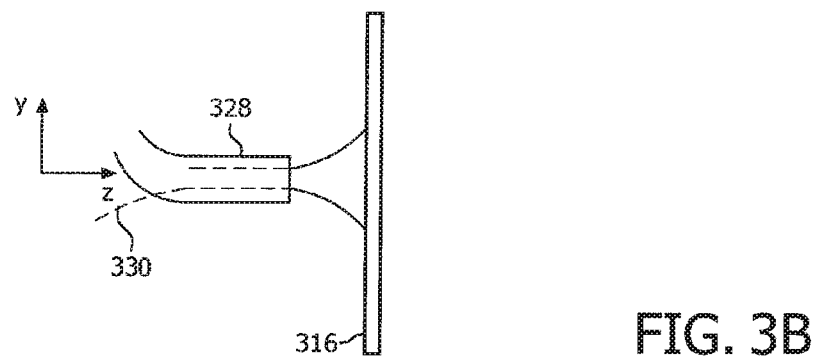

For easier visualization, an imaging plane or slice 330 may be acquired, as seen in FIG. 3B which shows a side view of the x/z plane. In this example, the tip longitudinally extends within the imaging plane 330.

For display, the tissue-specific and tool-specific frames can be fused together. A weighted average of the two frames may be used. Or, the tool-specific frame may be overlaid in a different color. Alternatively, in a dual display, the left screen could show the tissue-specific frame, with the right screen showing the tool-specific frame.

If the tip 328 is oblique to the imaging plane 330, one or more planes that contain the tip can be imaged, as discussed in an example further below, to afford more accurate display of the anatomy immediately surrounding the distal end of the tip.

Figure 3C:
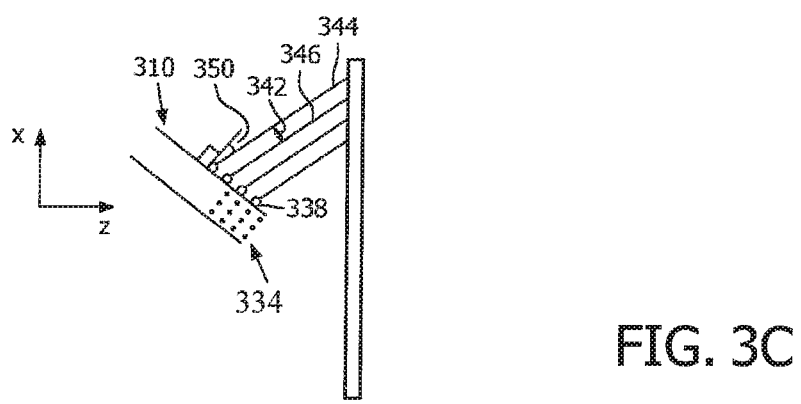

FIG. 3C illustrates an exemplary use of shape sensors 334, such as fiber Bragg gratings that are either stretched or compressed by an external stimulus, as an alternative or complement to the ultrasound sensors 304, 306. Here, the shape sensors 334 exist along optical fibers that run longitudinally along the catheter or other tool 310. The fibers, at a proximal end of the catheter 310, are connected to an optical frequency domain reflectometer (OFDR) (not shown) which is communicatively connected to the beamformer 308. Examples of shape sensors for medical instruments such as catheters are provided in U.S. Pat. No. 7,772,541 to Froggatt et al. (hereinafter "Froggatt"), the entire disclosure of which is incorporated herein by reference. As in Froggatt, the shape sensors 334 conform to at least a portion of the catheter 310 for sensing a shape of the portion. They also allow detection of positions, i.e., locations, at the sensors. Based on these measurements, the location 329 and the orientation 330 of the catheter 310 in the imaging space of the probe 302 are calculated. The beamformer 308 uses the estimate of the location 329 and orientation 330 in forming transmit foci 338 along the catheter 310. If the orientation of the catheter 310 is such that its image depth varies along the catheter, the transmit foci 338 are at different depths to conform to catheter. The transmit beam 344, 346 has the richest angular spectrum content at its focal depth, thus maximizing the probability of ultrasound reflection toward the probe 302. Beamforming is accordingly being optimized based on the pose estimate. Although the foci 338 are shown in FIG. 3C as existing on the exterior of the catheter 310, they may be placed elsewhere, in the radial center for example.

The spacing 342 between two transmit beams 344, 346 is shown in FIG. 3C. Interruptions, i.e., interruption artefacts, are sometimes visible along the elongated tool 310, such as a catheter or needle, and can be caused by destructive interference due to echoes from neighboring parts of the tool. The artefacts can be mitigated or eliminated by making spatial sampling of the transmit and/or receive beams finer, as shown by example further below.

Steered beams that insonify an imaged tool 310 with an angle of 60 to 90 degrees with respect to the tool's body, i.e., angle of incidence of 30 degrees or under, generate good reflections toward the probe 302. As seen in FIG. 3C, the angle of incidence 350 is within the 30 degree range. The good reflection toward the probe 302 provides an easily visible ultrasound image. The transmit and receive beam angles are optimized for tool reflectivity. The optimizing can include maximizing the coherence factor, i.e., ratio of coherently summed signals to incoherently summed signals, to thereby enhance visibility, reduce sidelobes and increase signal-to-noise ratio (SNR). Wiener filtering can be used in low SNR cases. Coherence factor and Weiner filtering techniques are discussed in U.S. Pat. No. 7,744,532 to Ustuner et al. and "Weiner Beamforming and Coherence Factor in Ultrasound Imaging", IEEE Transactions on Ultrasonics, Ferroelectrics, and Frequency Control, Vol. 57, No. 6, June 2010.

Figure 4:
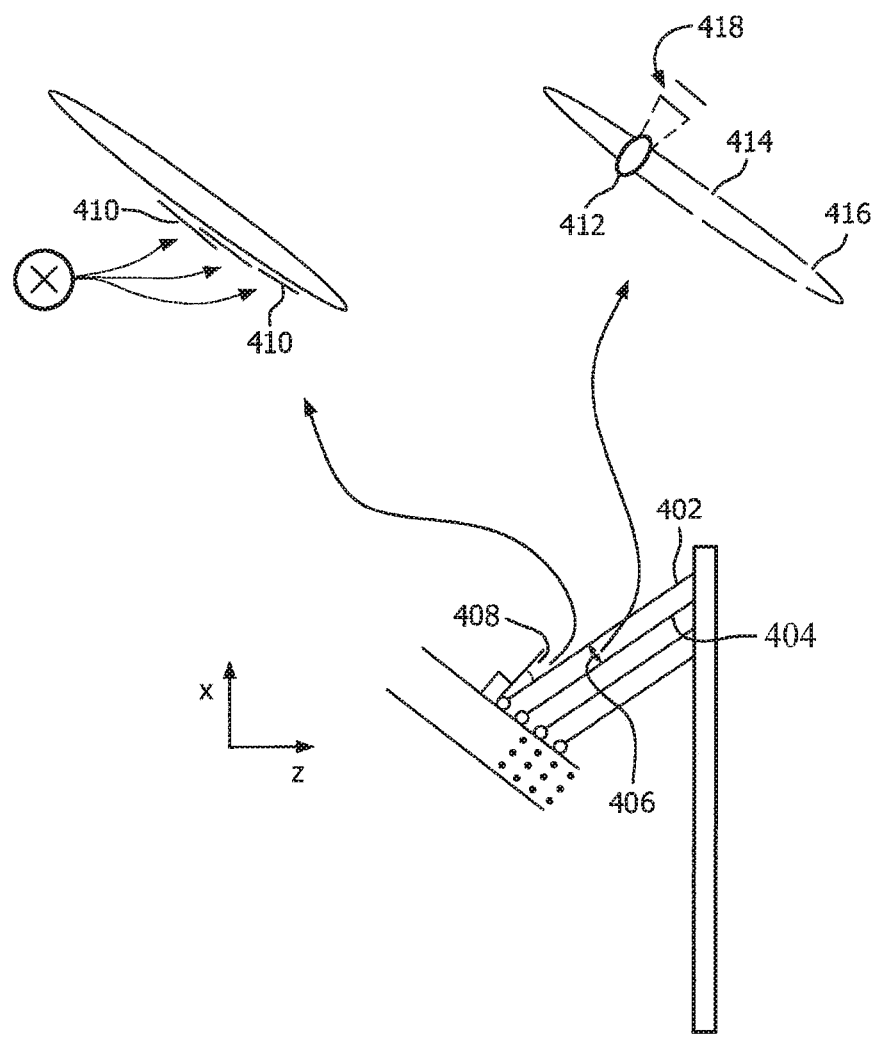
FIG. 4 is a schematic and conceptual diagram of beamforming parameter considerations in mitigating or eliminating visual artefacts.

The avoidance of a normal angle, i.e., exactly 90 degrees, between the tool body and the ultrasound beam can prevent or mitigate visual artefacts, as shown by example in FIG. 4. The beamformer 308 is accordingly configured for limiting an angle of incidence 408 of a transmit beam, a receive beam, or both, to a nonzero value to avoid sidelobe and reverberation artefacts. Thus, reverberation and sidelobe artefacts 410 are prevented or mitigated, this being represented by the circled "x."

In addition, receive beams 402, 404 are spaced apart by a spatial interval 406. The beam spacing 406 is spatially fine enough to mitigate or eliminate imaging artefacts discernible as interruptions 412, 414, 416 along the interventional tool 310. This is represented in FIG. 4 by the replacement of the interruption 412 with the missing image 418.

Figure 5A:
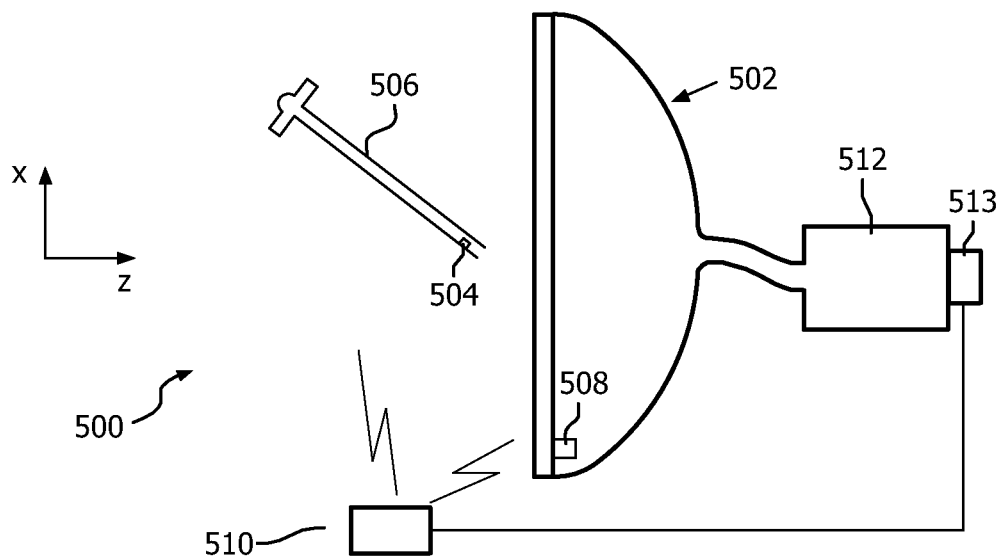
FIGS. 5A, 5B are schematic diagrams of electromagnetic- and optical-based sensor embodiments.

FIG. 5A illustrates an (electromagnetic) EM sensing-based ultrasound imaging device 500. It includes an ultrasound probe 502, an EM sensor (or "transducer") 504 attached to a needle 506 or other interventional medical tool, an EM sensor 508 attached to the probe, an EM field generator 510, a beamformer 512, and an estimation and initialization module 513. The EM field generator 510 generates a field that induces a current in the EM sensors 504, 508. The EM sensors are configured for wirelessly communicating a measure of the induced current to the EM field generator 510, which, in turn, is designed for receiving the measure. Based on the induced current, the location and orientation of the sensors 504, 508 with respect to the EM field generator 510 are calculated. The estimation and initialization module 513 makes this calculation, registers electromagnetic tracking space with an imaging space of the probe 502, and supplies the results to the beamformer 512. Based on the results, the beamformer 512 performs imaging in conjunction with a transducer array 514. An example of using EM sensors in tracking a medical tool is provided in commonly-owned U.S. Pat. No. 7,933,007 to Stanton et al. A similar system which also attaches to the tool an optical sensor is disclosed in commonly-owned U.S. Patent Publication No. 2010/0168556 to Shen et al. Both documents are incorporated herein by reference in their entirety. Although wireless communication of the induced current data is described herein above, the data may be conveyed by wires in the ultrasound probe 502 and wires running down the tool 506. Also, more than one EM sensor may be provided in the probe 502 and in the tool 506. By ultrasound imaging standards, the EM localization is a rough estimate. However, feedback with enhanced ultrasound beamforming according to what is proposed herein is used to fine tune the imaging of the object 506.

Figure 5B:
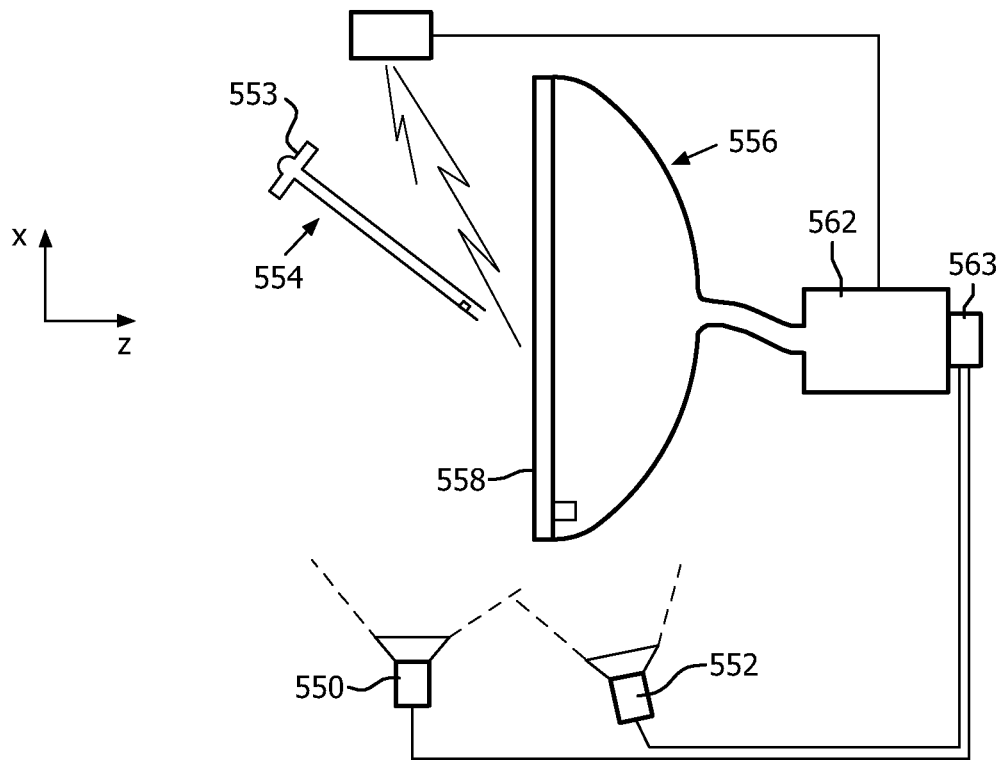

An image-based estimate approach, optionally enhanced by EM sensors, is shown in FIG. 5B. Two cameras 550, 552, serving as optical sensors, are aimed both at the base 553 of a needle 554 and at a probe 556, and are therefore disposed with respect to the needle for sensing its location/orientation. Indicia are provided around the periphery of the probe 556, near a transducer array 558, and optionally around the base 553 of the needle 554. The location and orientation of both cameras 550, 552, and images from the cameras, are supplied to an estimation and initialization module 563. From the imaged indicia, a location 329 of a rigid tool and the tool's orientation 330 may be estimated. Location and orientation data determined based on output of EM sensors 564, 566, as described in connection with FIG. 5A, is also supplied to the estimation and initialization module 563. The image based data may be used to update the EM-based data, and a pose estimate is registered with an image space of the beamformer 562. An example of this arrangement is found in commonly-owned U.S. Patent Publication No. 2010/0194879 to Pasveer et al., the entire disclosure of which is incorporated herein by reference.

Figure 6:
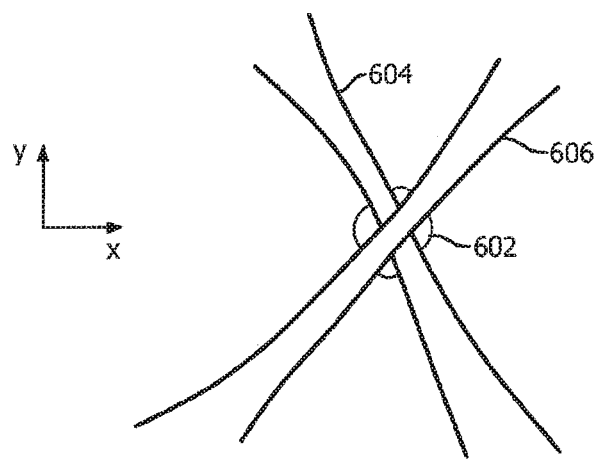
FIG. 6 is a conceptual diagram of imaging planes formed to contain an interventional tool in a longitudinal direction.

FIG. 6 shows a cross-section 602 of an interventional tool at least a tip of which longitudinally extends in two separate imaging planes 604, 606. This imaging is particularly useful when the tool extends obliquely to the target plane.

The oblique planes 604, 606 are acquired by use of an ultrasound probe with elevation steering capability, e.g., with a 2D or 1.75D imaging array. Incrementally, in real time, the elevation is varied plane by plane, to create a "thick slice." Thick slice acquisition is alternated or otherwise interspersed, in real time, with acquisition of the target plane data. The thick slice is acquired in the tool-specific frame, and the target plane data is acquired in the tissue-specific frame. From the acquired thick slice, image data corresponding to the oblique plane(s) desired is extracted.

Tissue-specific content of the target plane can be displayed to the user, with one or more of the oblique imaging planes 604, 606, specifically the tool-specific content thereof, alongside. Or, a projection of the tool can be overlaid on the target plane. On the display, an indicator of the relative orientation of the planes can be included. The indicator could, for example, be a schematic of an imaging probe and, extending from it, the two oblique planes 604, 606, illustrating their relative positions to each other.

Figure 7:
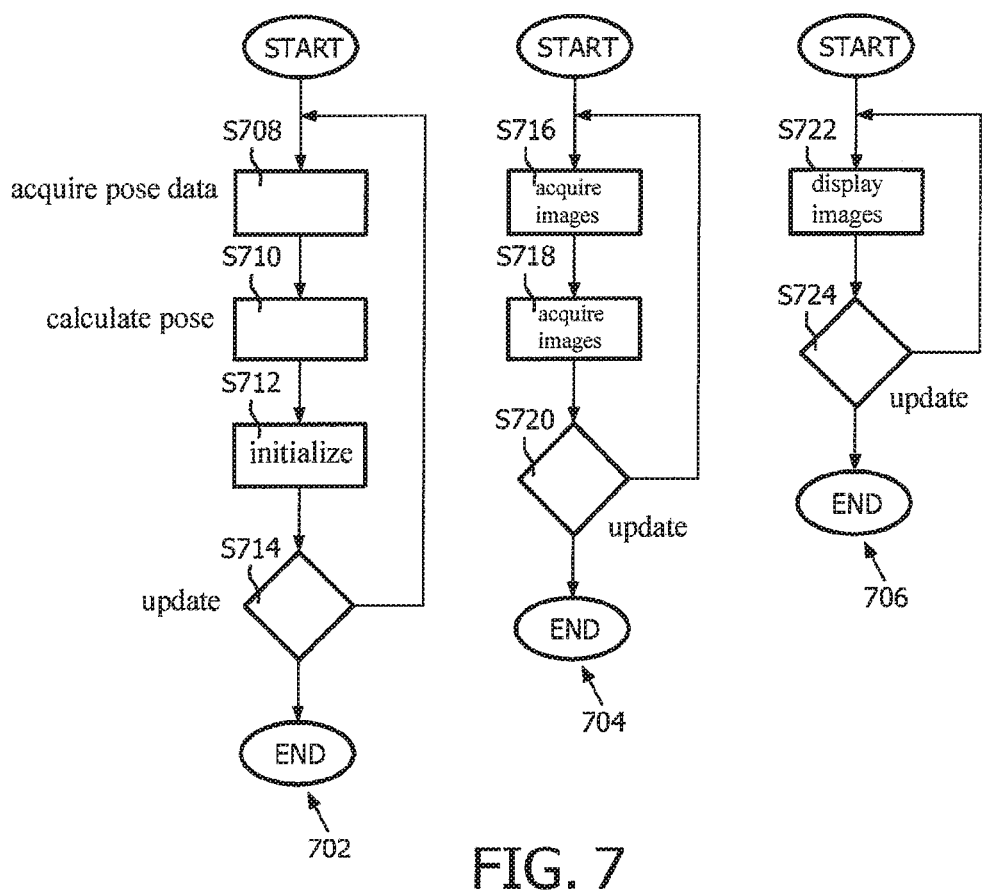
FIG. 7 consists of three flow charts on beamformer initialization, imaging data acquisition, and imaging data display, respectively.

FIG. 7 consists of flow charts of exemplary processes of beamformer initialization 702, imaging data acquisition 704, and imaging data display 706, respectively.

According to the beamformer initialization process 702, pose data is acquired (step S708). From the acquired pose data, the pose, i.e., location 329 and orientation 330, is calculated (step S710). The beamformer is initialized with the calculated pose (step S712). If initialization is to be updated (step S714), as will typically occur in real time, processing returns to step S708.

In the concurrent data acquisition process 704, the estimated pose is used to acquire one or more tool-specific images (step S716). A tissue-specific image is then acquired (step S718). If imaging data acquisition is to be updated (step S720), as will typically occur in real time, processing returns to step S716.

In the also concurrent data display process 706, display is made of the current acquired imaging data (step S722). The display may include one tool-specific image, alongside a tissue-specific image. If the tool is oblique to the target plane, one or more tool-containing planes 604, 606, specifically the tool-specific content thereof, may instead be placed alongside the target plane, specifically the tissue-specific content thereof, along with an indication of the relative orientations of the planes. If the image display is to be updated (step S724), as will typically occur in real time, processing returns to step S722.

Beamforming to image an object, such as an interventional tool, is enhanced by initializing the beamformer with the object's location, and optionally its orientation. The initializing uses an estimate of the location/orientation. The estimate is derived from the output of one or more sensors. These are disposed external to the imaging array that operates with the beamformer. The estimate is made without the need for a result of any imaging based on data arriving by reflected ultrasound. One or more of the sensors may be attached to the object, which may be elongated, as in the case of a needle or catheter used in medical diagnosis and treatment. In some implementations, one or more of the sensors are attached to the imaging probe. The sensors may be, for example, ultrasound, electromagnetic, optical, or shape sensors. Alternatively, ultrasound transmitting transducers may be substituted for the ultrasound sensors.

The clinical applications of the novel technology discussed herein above include any procedure where determining the location and orientation of a surgical tool is desirable and cannot reliably be performed with standard ultrasound imaging alone.

Although the novel apparatus and methodology can advantageously be applied in providing medical diagnosis or treatment for a human or animal subject, the intended scope of claim coverage is not so limited. More broadly, enhanced imaging, in vivo, in vitro or ex vivo is envisioned.

While the invention has been illustrated and described in detail in the drawings and foregoing description, such illustration and description are to be considered illustrative or exemplary and not restrictive; the invention is not limited to the disclosed embodiments.

For example, the elongated tool may be an applicator for radioactive seed insertion in treating cancer. As another example, on a tool with multiple ultrasound tracking transducers, the type can be mixed, with some transmitters and others receivers. Also, mixing of sensor types in a single embodiment can involve ultrasound, shape, EM, optical or other types of sensors.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An ultrasound system, comprising:
an ultrasound transducer array configured to transmit ultrasound signals to a sensor on an object for deriving a location and an orientation of the object;
a beamformer coupled to the ultrasound transducer array; and
a processor configured to receive an output of the sensor, to derive a tool-pose-estimation of the object including the location and the orientation of the object, and to provide the tool-pose-estimation to the beamformer,
wherein the ultrasound transducer array repeatedly transmits the ultrasound signals to the sensor in a one-way beamforming process for deriving the location and the orientation of the object;
wherein the processor operates with the beamformer and the ultrasound transducer array in the one-way beamforming process to repeatedly: acquire initialization frames, localize the sensor in a coordinate system based on the initialization frames, derive the tool-pose-estimation of the object based on localizing the sensor in the coordinate system, and initialize the beamformer with respect to tool-specific imaging frames based on the tool-pose-estimation;
wherein the ultrasound transducer array repeatedly transmits ultrasound signals in a two-way beamforming process, concurrent with the one-way beamforming process, wherein the transmissions in the two-way beamforming process are interspersed with the acquisitions of initialization frames in the one-way beamforming process; and
the processor operates with the initialized beamformer and the ultrasound transducer array based on the two-way beamforming to alternately acquire the tool-specific imaging frames and tissue-specific imaging frames using pulse-echo imaging, in the coordinate system.

2. The ultrasound system of claim 1, wherein the processor derives the tool-pose-estimation without need for a result of any imaging based on data arriving by reflected ultrasound.

3. The ultrasound system of claim 1, further comprising: the object and the sensor, wherein the sensor is attached to the object.

4. The ultrasound system of claim 3, further comprising: at least one additional sensor located apart from the sensor, wherein the object comprises the sensor and the at least one additional sensor.

5. The ultrasound system of claim 1, further comprising: the object, the sensor and a further sensor, wherein the object comprises an elongated body and the further sensor conforms to at least a portion of the elongated body.

6. The ultrasound system of claim 1, further comprising: the object, the sensor and a further sensor, wherein the object comprises a tool being rigid and having a base and the further sensor is configured to optically detect the base for deriving the tool-pose-estimation by the processor.

7. The ultrasound system of claim 1, wherein the beamformer is configured to limit an angle of incidence of at least one of a transmit beam and a receive beam to a nonzero value to mitigate sidelobe and reverberation artefacts.

8. The ultrasound system of claim 1, wherein the object is elongated, and wherein the beamformer is further configured to, based on the tool-pose-estimation, place a plurality of transmit foci along the object at different depths to conform to the object.

9. The ultrasound system of claim 1, wherein the object is elongated, wherein the beamformer is configured to steer ultrasound signals in an elevation direction, and wherein the initializing of the beamformer causes operation of the ultrasound transducer array to image an imaging plane in which a tip of the object longitudinally extends.

10. The ultrasound system of claim 9, wherein the tip longitudinally extends within a further imaging plane, wherein the imaging plane and the further imaging plane are mutually non-parallel, the beamformer being further configured by the processor to operate the ultrasound transducer array to acquire images in the imaging plane and the further imaging plane for concurrent display of the images in real time on a display.

11. The ultrasound system of claim 1, wherein the object is elongated, and wherein the beamformer is configured to spatially space beams to mitigate imaging artefacts discernible as interruptions along the object within an image of the object.

12. The ultrasound system of claim 1, wherein the location comprises a tip of the object, and the tool-pose-estimation comprises an estimate of the location.

13. The ultrasound system of claim 1, wherein the processor is further configured to perform the deriving of the tool-pose-estimation, and to initialize the beamformer in real time to track the object.

14. The ultrasound system of claim 1, further comprising: the object, wherein the object comprises a specular reflector of ultrasound.

15. The ultrasound system of claim 1, wherein the ultrasound transducer array repeatedly transmits the ultrasound signals in a first frequency band to the sensor in the one-way beamforming process for deriving the location and the orientation of the object, and wherein the ultrasound transducer array repeatedly transmits the ultrasound signals in a second frequency band, separate and apart from the first frequency band, in the two-way beamforming process.

16. A beamforming method for enhancing visualization of an object comprising at least one sensor, the method comprising:
repeatedly transmitting, by an ultrasound transducer array, ultrasound signals to the at least one sensor in a one-way beamforming process;
repeatedly acquiring initialization frames by a processor operating with the ultrasound transducer array in the one-way beamforming process;
repeatedly localizing the at least one sensor in a coordinate system based on the initialization frames;
repeatedly deriving a tool-pose-estimation comprising an estimate of a location and an orientation of the object by the processor based on localizing the at least one sensor in the coordinate system;
repeatedly initializing, with respect to tool-specific imaging frames and based on the tool-pose-estimation, a beamformer as an initialized beamformer for operating with the ultrasound transducer array to place a transmit focus at the object;
repeatedly transmitting, by the ultrasound transducer array, ultrasound signals in a two-way beamforming process, wherein the two-way beamforming process is concurrent with the one-way beamforming process, and wherein the transmissions of ultrasound signals in the two-way beamforming process are interspersed with the transmissions of the ultrasound signals in the one-way beamforming process; and
operating the ultrasound transducer array with the initialized beamformer and the processor based in the two-way beamforming process to alternately acquire the tool-specific imaging frames and tissue-specific imaging frames using pulse-echo imaging, in the coordinate system,
wherein the tool-specific imaging frames are for acquisition of images of the object and the tissue-specific imaging frames are for acquisition of images of a region of interest.

17. The method of claim 16:
wherein repeatedly transmitting, by the ultrasound transducer array, the ultrasound signals to the at least one sensor in the one-way beamforming process comprises repeatedly transmitting, by the ultrasound transducer array, the ultrasound signals to the at least one sensor in the one-way beamforming process in a first frequency band, and
wherein repeatedly transmitting, by the ultrasound transducer array, the ultrasound signals in the two-way beamforming process comprises repeatedly transmitting, by the ultrasound transducer array, the ultrasound signals in the two-way beamforming process in a second frequency band, separate and apart from the first frequency band.

18. A non-transitory computer-readable medium embodying computer instructions which, when executed by a processor, configure the processor to perform acts of:
repeatedly transmitting, by an ultrasound transducer array, ultrasound signals to at least one sensor in a one-way beamforming process;
repeatedly acquiring initialization frames by a processor operating with the ultrasound transducer array in the one-way beamforming process;
repeatedly localizing the at least one sensor in a coordinate system based on the initialization frames;
repeatedly deriving a tool-pose-estimation comprising an estimate of a location and an orientation of an object, having at least one sensor, based on localizing the at least one sensor in the coordinate system;
repeatedly initializing, with respect to tool-specific imaging frames and based on the tool-pose-estimation, a beamformer for operating with an ultrasound transducer array to place a transmit focus at the object;
repeatedly transmitting, by the ultrasound transducer array, ultrasound signals in a two-way beamforming process, wherein the two-way beamforming process is concurrent with the one-way beamforming process, and wherein the transmissions of ultrasound signals in the two-way beamforming process are interspersed with the transmissions of ultrasound signals in the one-way beamforming process; and
operating the ultrasound transducer array with the initialized beamformer and the processor in the two-way beamforming process to alternately acquire the tool-specific imaging frames and tissue-specific imaging frames using pulse-echo imaging, in the coordinate system,
wherein the tool-specific imaging frames are for acquisition of images of the object and the tissue-specific imaging frames are for acquisition of images of a region of interest.

19. An ultrasound system, comprising:
an ultrasound transducer array configured to transmit ultrasound signals to a sensor on an object for deriving a position of the object;
a beamformer coupled to the ultrasound transducer array; and
a processor configured to receive an output of the sensor, to derive a tool-pose-estimation of the object including the position of the object, and to provide the tool-pose-estimation to the beamformer,
wherein, the ultrasound transducer array repeatedly transmits the ultrasound signals to the sensor in a one-way beamforming process for deriving the position of the object;
wherein the processor operates with the beamformer and the ultrasound transducer array in the one-way beamforming process to repeatedly, acquire initialization frames, localize the sensor in a coordinate system based on the initialization frames, derive the tool-pose-estimation of the object based on localizing the sensor in the coordinate system, and initialize the beamformer with respect to tool-specific imaging frames based on the tool-pose-estimation;
wherein the ultrasound transducer array repeatedly transmits ultrasound signals in a two-way beamforming process, concurrent with one-way beamforming process and wherein the transmissions in the two-way beamforming process are interspersed with the acquisitions of the initialization frames in the one-way beamforming process; and
wherein the processor operates with the initialized beamformer and the ultrasound transducer array based on the two-way beamforming to alternately acquire the tool-specific imaging frames and tissue-specific imaging frames using pulse-echo imaging, in the coordinate system.

20. The ultrasound system of claim 19, wherein the ultrasound transducer array repeatedly transmits the ultrasound signals in a first frequency band to the sensor in the one-way beamforming process for deriving the location and the orientation of the object, and wherein the ultrasound transducer array repeatedly transmits the ultrasound signals in a second frequency band, separate and apart from the first frequency band, in the two-way beamforming process.

* * * * *